United States Patent
Rubey et al.

(10) Patent No.: US 8,279,059 B2
(45) Date of Patent: Oct. 2, 2012

(54) DATA RECORDER, SYSTEM AND METHOD FOR TRANSMITTING DATA RECEIVED FROM AN IN-VIVO SENSING DEVICE

(75) Inventors: Kevin Rubey, Ventura, CA (US); Ido Bettesh, Haifa (IL); Eli Horn, Kiryat Motzkin (IL); Micha Nisani, Nesher (IL); Boaz Aizenshtark, Shimshit (IL); Alexander Veinblat, Haifa (IL); Avidor Rabinovich, Kiryat Motzkin (IL); Uri Kogan, Nesher (IL); Pesach Pascal, Nesher (IL)

(73) Assignee: Given Imaging Ltd., Yoqneam (IL)

( * ) Notice: Subject to any disclaimer, the term of this patent is extended or adjusted under 35 U.S.C. 154(b) by 575 days.

(21) Appl. No.: 12/344,953

(22) PCT Filed: Jul. 1, 2007

(86) PCT No.: PCT/IL2007/000810
§ 371 (c)(1),
(2), (4) Date: Oct. 19, 2009

(87) PCT Pub. No.: WO2008/001387
PCT Pub. Date: Jan. 3, 2008

(65) Prior Publication Data
US 2010/0052895 A1   Mar. 4, 2010

Related U.S. Application Data

(60) Provisional application No. 60/817,094, filed on Jun. 29, 2006.

(51) Int. Cl.
*G08B 1/08* (2006.01)

(52) U.S. Cl. .............. 340/539.1; 340/506; 340/539.13; 340/539.12; 340/573.1

(58) Field of Classification Search ............ 340/506, 340/539.1, 539.13, 539.12
See application file for complete search history.

(56) References Cited

U.S. PATENT DOCUMENTS

| | | | |
|---|---|---|---|
| 5,959,529 A * | 9/1999 | Kail, IV | 340/539.12 |
| 6,270,457 B1 | 8/2001 | Bardy | |
| 6,402,689 B1 | 6/2002 | Scarantino et al. | |
| 6,577,899 B2 | 6/2003 | Lebel et al. | |
| 6,804,558 B2 | 10/2004 | Haller et al. | |
| 7,978,062 B2 * | 7/2011 | Lalonde et al. | 340/539.11 |

OTHER PUBLICATIONS

Search Report from International Application No. PCT/IL07/00810 mailed on May 28, 2008.

* cited by examiner

*Primary Examiner* — Daryl Pope
(74) *Attorney, Agent, or Firm* — Pearl Cohen Zedek Latzer, LLP

(57) ABSTRACT

An in-vivo sensing system including an in-vivo sensing device, a data recorder a receiver and a work station. The data recorder receives data signal from the in-vivo sensing device during an acquisition period. Batches of the data signal may be transmitted from the data recorder to a receiver, as soon as a batch has been received by the data recorder. The batches of data signal received by the receiver may be downloaded to the workstation as soon as each batch is received by the receiver. Signals are typically transmitted from the data recorder to the receiver through wireless transmission techniques such as cellular transmission, WLAN (Wireless Local Area Network) transmission, BT (BlueTooth) transmission and Wimax (Worldwide interoperability for Microwave Access) transmission.

9 Claims, 2 Drawing Sheets

DATA RECORDER, SYSTEM AND METHOD FOR TRANSMITTING DATA RECEIVED FROM AN IN-VIVO SENSING DEVICE

CROSS-REFERENCE TO RELATED APPLICATIONS

This application is a National Phase Application of PCT International Application No. PCT/IL2007/000810, International Filing Date Jul. 1, 2007, entitled "Data Recorder, System and Method for Transmitting Data Received from an In-Vivo Sensing Device" published on Jan. 3, 2008 as International Publication Number WO 2008/001387 which in turn claims priority from U.S. Provisional Patent Application No. 60/817,094, filed Jun. 29, 2006, both of which are incorporated herein by reference in their entirety.

FIELD OF THE INVENTION

The present invention relates in general to a data recorder for receiving data transmitted by an in-vivo sensing device. More specifically, the present invention relates to a method of transmitting the received data by the data recorder.

BACKGROUND OF THE INVENTION

In-vivo sensing devices for diagnosis of the gastrointestinal (GI) tract of a patient such as, for example, ingestible sensing capsules may wirelessly transmit sensed data, such as imaging data, to an external data recorder. The data recorder may be affixed to the patient by a strap or a belt so that the patient may freely perform normal actions during an observation period that may begin after swallowing of the in-vivo sensing device and may end upon its excretion. The data recorder may have radio communication capability and it may have connected to it one or more antennas for receiving the sensed data transmitted by the in-vivo sensing device and the data recorder may have a memory for storing the received sensed data.

After the observation period, the patient may deliver the data recorder to an operator, for example, a health professional who may be located at a health center and who may download the stored sensed data for processing and for performing analysis of the GI tract for diagnosis purposes. The sensed data may include image data of images of the GI tract captured by an imager in the in-vivo sensing device as it passes through the GI tract. The patient may be unable to get to the health center. In some cases the patient may be remotely located with respect to the health center. Instead of delivering the data recorder to the operator, the stored sensed data may be transmitted by telephone or by internet or by any other wire/wireless link by the patient to the health center. This may require that the patient be capable of operating suitable transmitting equipment.

SUMMARY OF THE INVENTION

According to embodiments of the present invention, a data signal transmitted by an in-vivo sensing device to a data recorder may be transmitted by the data recorder to a receiver and then downloaded to a workstation. The data signal may include sensed data such as image data captured by an imager in the in-vivo sensing device. The receiver may be at a remote location in relation to the data recorder and the workstation may be at a remote location in relation to the receiver and in relation to the data recorder.

The data recorder receives the data signal from the in-vivo sensing device during an acquisition period. The in-vivo sensing device may be traversing the gastrointestinal tract or other body lumens or cavities of a patient and the acquisition period may be the total time that the in-vivo sensing device acquires sensed data of the gastrointestinal tract or other body lumens or cavities of the patient. Batches of the data signal may be transmitted from the data recorder to a receiver, as soon as, or soon after, a batch of data signal has been received by the data recorder. The batches of data signal received by the receiver may be downloaded to the workstation as soon as, or soon after, each batch is received by the receiver. In some embodiments, the receiver and the workstation may be integrated into a single unit.

BRIEF DESCRIPTION OF THE DRAWINGS

The present invention will be understood and appreciated more fully from the following detailed description taken in conjunction with the drawings in which.

Figure 1:
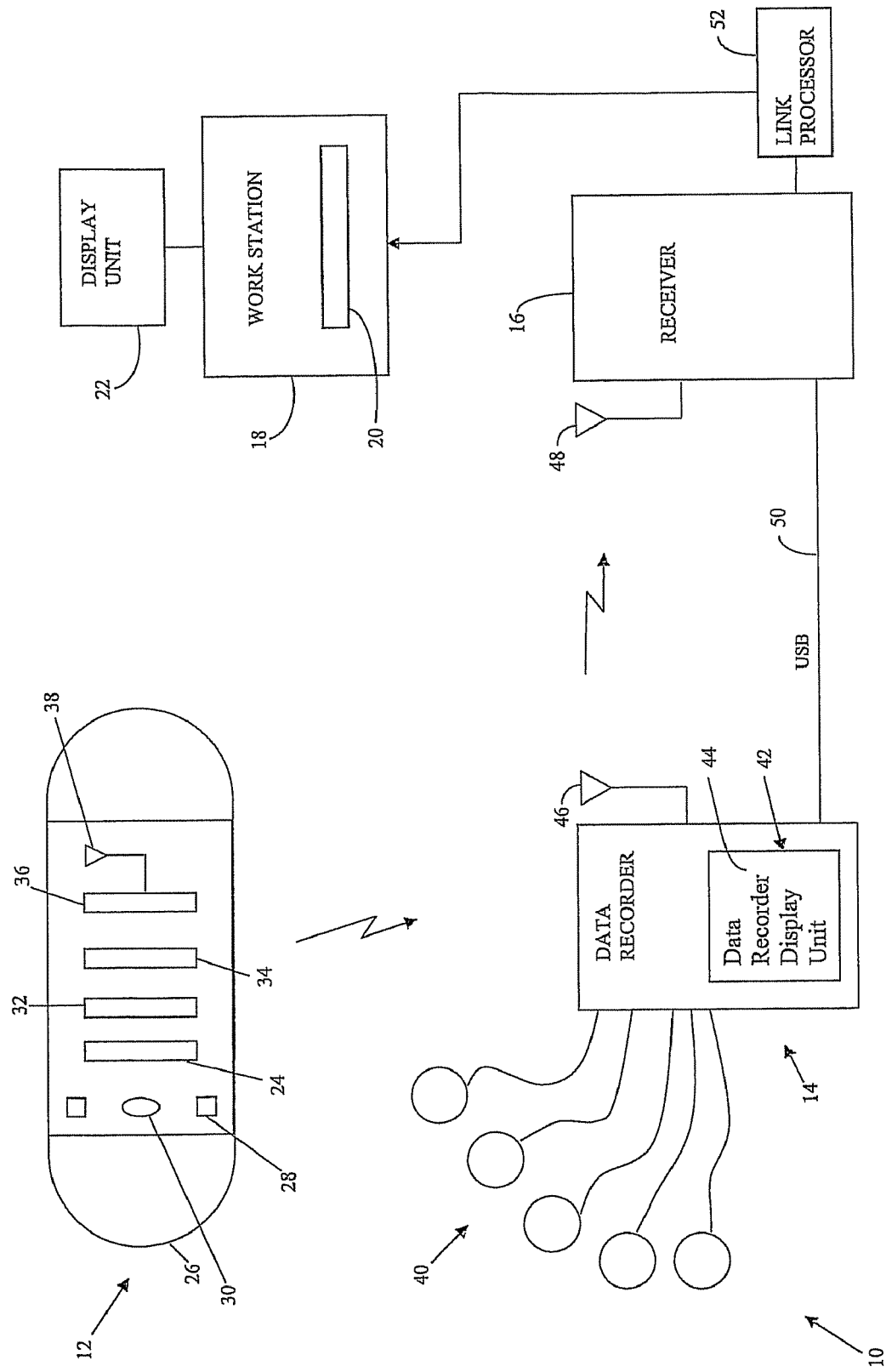
FIG. 1 is a simplified conceptual illustration of a system for transmitting data received from an in-vivo sensing device according to embodiments of the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

The device, system and method of the present invention may be used with an imaging system or device such as that described in U.S. Pat. No. 5,604,531 entitled "In Vivo Video Camera System," which is incorporated herein by reference. A further example of an imaging system and device with which the system and method of the present invention may be used is described in U.S. Pat. No. 7,009,634 entitled "Device for In Vivo Imaging," which is incorporated herein by reference. For example, a swallowable imaging capsule such as that described in U.S. Pat. No. 7,009,634, may be used in the present invention.

Reference is made to FIG. 1, showing in-vivo sensing system 10 according embodiments of the present invention. The in-vivo sensing system 10 includes an in-vivo sensing device 12, a data recorder 14 an optional additional, possibly remote, receiver 16 and a work station 18 having a work station processor 20 and a display unit 22. In some embodiments, the receiver 16 and the work station 18 may be integrated into a single unit. For example, may be integrated into a single portable unit.

In some embodiments, the in-vivo sensing device 12 may be a wireless device. In some embodiment, the in-vivo sensing device 12 may be autonomous. In some embodiments, the in-vivo sensing device 12 may be a swallowable capsule for sensing the gastrointestinal tract of a patient. However, other body lumens or cavities may be sensed or examined with the in-vivo sensing device 12.

The in-vivo sensing device 12 may include at least one sensor such as an imager 24 for capturing image data in the form of image frames of images of the gastrointestinal tract or other body lumens or cavities, a viewing window 26, one or more illumination sources 28, an optical system 30, a power supply such as a capsule battery 32, a capsule processor 34, a capsule transmitter 36, and a capsule antenna 38 connected to the capsule transmitter 36. The imager 24 may be and/or contain a CMOS imager. Alternatively, other imagers may be used, e.g. a CCD imager or other imagers. As the in-vivo sensing device 12 traverses the gastrointestinal tract or other body lumens, it takes images thereof at a rate of a given number of frames per second and over a given acquisition period. The series of images captured by the imager 24 of the in-vivo sensing device 12 form frames of a video movie.

The image data and or other data, captured by the in-vivo sensing device 12 during the acquisition period may be transmitted as a data signal by wireless connection, e.g. by wireless communication channel, from the in-vivo sensing device 12 and received by the data recorder 14 via one or more data recorder receiving antennas 40, for example an antenna array that may, for example, be removably attached to the patient's body, at least partially surrounding the patient's body. The hand-held data recorder 14 may include a data recorder display unit 42 having a liquid crystal (LCD) display 44.

The data signal received by the data recorder 14 may be transmitted from the data recorder 14 to the receiver 16. The receiver 16 may be located in the vicinity of the data recorder 14 or at a remote location. The data signal received by the data recorder 14 may be transmitted to the receiver 16 via cable using a USB connection, Internet link or any other point-to-point or point-to-multi point connection. The data signal received by the data recorder 14 may be transmitted to the receiver 16 by wireless connection, e.g. by wireless communication channel. Wireless transmission may be, for example, by any one of the following technologies: cellular transmission, WLAN (Wireless Local Area Network) transmission, BT (BlueTooth) transmission and Wimax (Worldwide interoperability for Microwave Access) transmission. The receiver 16 may be a receiver capable of operating in accordance with the aforementioned technologies.

The data signal received by the receiver 16 may be downloaded to the work station 18 for processing by the work station processor 20, and for analysis, and display, for example, by the display unit 22. The data signal may be downloaded from the receiver 16 to the work station 18, for example, by telephone via a land telephone line, or via an internet connection between the receiver 16 and the data recorder 14. The link used for downloading from the receiver 16 to the workstation 18 is controlled by a link processor 52. The receiver 16 may act as a central server from which the data signal received by the receiver 16 may be retrieved by a third party. The received data signal may undergo processing at the receiver 16. The third party may retrieve the processed data signal. The receive module can be part of the work station, or even a software module on the work station.

According to some embodiments the receiver 16 is not necessary. In-vivo data received and recorded by the data recorder 14 may be downloaded from the data recorder 14 directly to the work station 18 for processing and later viewing by a health professional.

Figure 2:
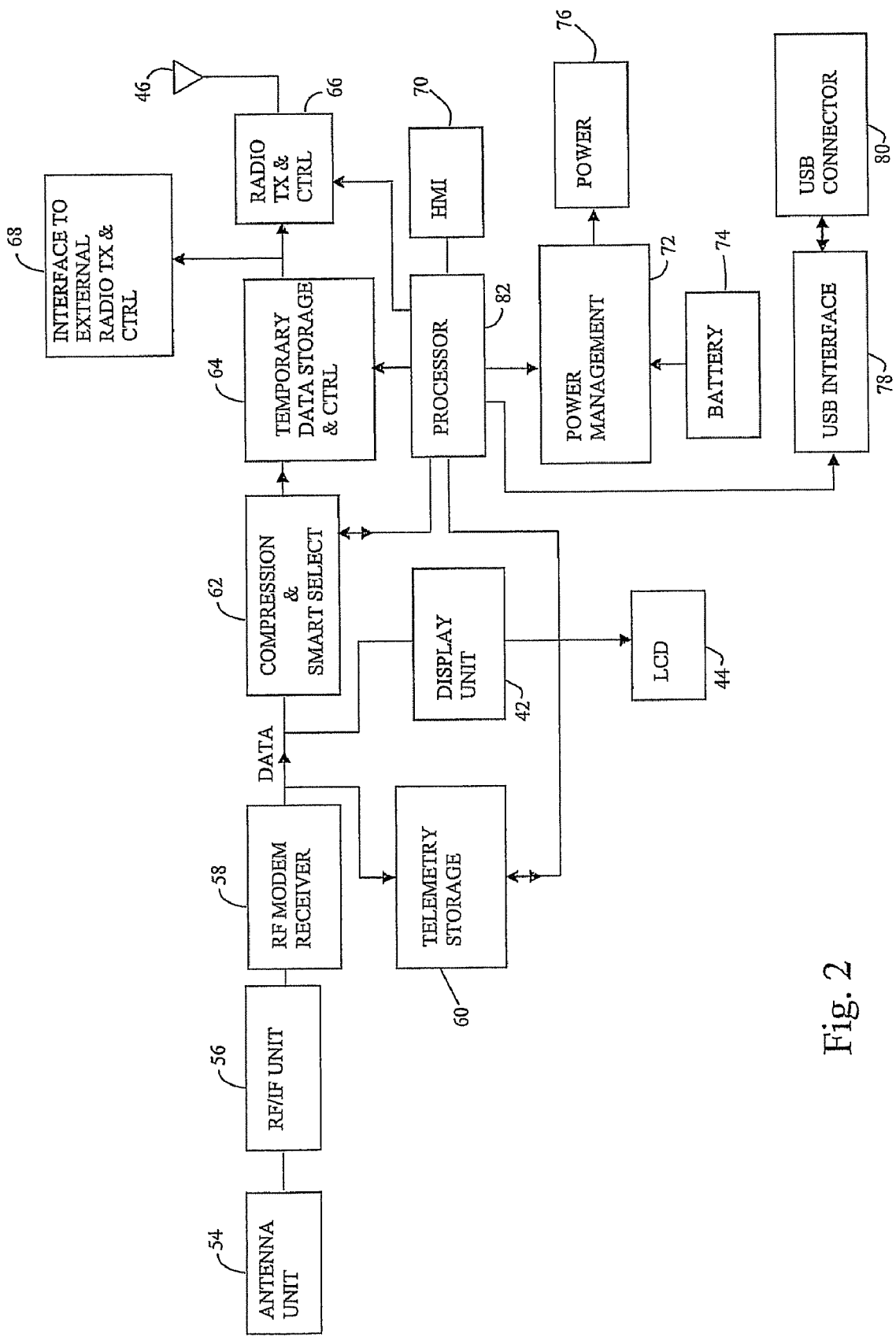
FIG. 2 is an illustrative block diagram showing components of a data recorder in accordance with some embodiments of the present invention.

Reference is now made to FIG. 2. The data recorder 14 may include an antenna unit 54 to which the data recorder receiving antenna 40 may be connected. Connected to the antenna unit 54 is an RF/IF unit 56 followed by a radio frequency (RF) modem receiver 58. The output of the RF modem 58 is data bits which may be inputted to a telemetry storage unit 60 for storing telemetry information in the received data signal. A compression unit 62 may be included for compressing the data bits. Compression unit 62 may be in some embodiments part of a compression-decompression unit. The compression unit 62 may have "smart select" capability so that image frames that match certain given criteria may not be compressed and may not be transmitted by the data recorder 14. The data recorder 14 may include a temporary data storage and control unit 64 that contains a memory and associated control logic for temporarily storing a given number of image frames and/or other data received from the in-vivo sensing device 12 and for controllably interfacing the stored data with other units of the data recorder 14. The temporary data storage and control unit 64 may be connected to a radio transmitter and control unit 66 integral with the hand-held data recorder 14, that is, an internal unit. The temporary data storage and control unit 64 may be connected communicate with an interface to an external radio transmitter and control unit 68. For both the internal and external radio transmitters, the radio transmitter may operate as a transmitter for at least any one of the following technologies: cellular transmission, WLAN (Wireless Local Area Network) transmission, BT (BlueTooth) transmission and Wimax (Worldwide interoperability for Microwave Access) transmission. In an alternative embodiment this link may be accomplished by a wire link, such as a wire Internet link.

The data recorder 14 may have various human machine interface (HMI) functions 70 for controlling the data recorder 14, including for example interfaces such as keyboards, touch-screens and pushbuttons. A power management unit 72, connected to a power source such as a data recorder battery 74, manages and provides power 76 to the units of the data recorder 14. A USB interface 78 and a USB connector 80 enables data transmission via the cable 50. A data recorder processor 82, connected to the various units as shown in FIG. 2, provides overall control of the hand-held data recorder 14 and provides required processing capability.

The data signal received by the data recorder 14 from the in-vivo sensing device 12 may be transmitted from the data recorder 14 to the receiver 16 intermittently in batches of image frames and other data during the acquisition period. For example, image frames received by the data recorder 14 from the in-vivo sensing device 12 may be stored in the temporary data storage unit 64 until a batch of image frames has been received and stored. The batch of temporarily stored image frames may then be transmitted to the receiver 16. The receiver 16 may then transmit the received batch of image frames to the workstation 18. In this manner, batches of image frames may be transmitted from the data recorder 14 to the receiver 16 intermittently, in real time or in quasi real time, each time the number of image frames stored in the temporary data storage unit 64 reaches a specified number of image frames constituting the batch. For example, from the beginning of the acquisition period, the image frames received by the data recorder 14 from the in-vivo sensing device 12 are temporarily stored in the temporary data storage unit 64 until a first batch of N image frames is acquired, where N is a real number (1, 2, 3, 4 . . . ). The first batch of N image frames is then transmitted to the receiver 16. Following this, a second batch of N image frames is received by the data recorder 14 and temporarily stored in the temporary data storage unit 64 before being transmitted to the receiver 16, and so on until the end of the acquisition period. In this way a batch of N image frames may be transmitted from the data recorder 14 to the receiver 16 every T minutes, where T is a real positive number.

According to some embodiments the number of frames does not have to be the same in each batch, other parameters could be used to determine when to transmit a batch of image frames.

According to some embodiments, the receiver 16 may receive and store all the image frames received from the data recorder 14 until the completion of the acquisition period and consequently download the data signal comprising all the image frames to the workstation 18.

According to some embodiments, the receiver 16 may download image frames to the workstation 18 intermittently in batches of N image frames. For example, image frames received by the receiver 16 from the data recorder 14 may be temporarily stored until the number of images reaches a given number of image frames defining a batch. Each time the number of image frames stored in the receiver 16 reaches a batch, the batch is downloaded to the workstation 18.

According to some embodiments, downloading from the receiver 16 to the workstation 18 may occur off-line for example after the receiver 16 has completed receiving and storing the data signal received from the data recorder 14. That is, the receiver 16 may receive and store all the batches of image frames and other data received from the data recorder 14 during the acquisition period and only download the stored image frames and other data to the workstation 18 after all the image frames and other data have been received from the data recorder 14.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the scope of the invention.

The invention claimed is:

1. A method for transmitting data by an in-vivo sensing device comprising:

sensing an in-vivo region of a body lumen by an in-vivo sensing device to produce sensed data during an acquisition period;

capturing said sensed data by the in-vivo sensing device;

transmitting the captured data by the in-vivo sensing device and receiving the transmitted data by a data recorder;

temporarily storing the received data in the data recorder until a specified amount of data has been stored, wherein said specified amount of data constitutes a batch of data;

transmitting the batch of data by the data recorder in real time to a workstation; and processing the batch of data in the workstation.

2. The method according to claim 1, wherein the sensed data includes image frames.

3. The method according to claim 1, comprising determining when to transmit a batch of stored data.

4. A system for transmitting in-vivo data comprising:

an in-vivo sensing device to sense an in-vivo region of a body lumen, said in-vivo device comprising a sensor and a transmitter;

a data recorder to receive in-vivo data from the in-vivo device, said data recorder comprising a storage unit for temporarily storing a batch of received data and a transmitter to transmit the batch of received data in real time; and a workstation comprising a receiver to receive the data batch and a processor to process it.

5. The system according to claim 4 wherein the data recorder comprises a compression unit to compress the in-vivo data.

6. The system according to claim 5 wherein the compression unit comprises a smart-select unit to select image frames for transmission to the workstation.

7. The system according to claim 4 wherein the data recorder comprises a telemetry storage unit for storing telemetry information of a received data signal.

8. The system according to claim 4 further comprising a receiver, wherein said receiver is to receive data from the data recorder and to transmit it to the workstation, said receiver comprising a processor for processing the data before transmitting it to the workstation.

9. The system according to claim 4 wherein the data recorder is hand-held.

* * * * *